United States Patent [19]

Ellman et al.

[11] Patent Number: 5,304,763

[45] Date of Patent: Apr. 19, 1994

[54] FINGER SWITCH FOR ELECTROSURGICAL HANDPIECE

[76] Inventors: Alan Ellman; Jon C. Garito, both of 1135 Railroad Ave., Hewlett, N.Y. 11557

[21] Appl. No.: 991,879

[22] Filed: Dec. 16, 1992

Related U.S. Application Data

[62] Division of Ser. No. 711,860, Jun. 7, 1991, Pat. No. 5,196,007.

[51] Int. Cl.[5] ............................................. H01H 13/04
[52] U.S. Cl. .................................... 200/295; 200/293.1; 200/332.2; 200/505; 200/DIG. 2
[58] Field of Search ................... 200/332.2, 331, 332.1, 200/293.1, 516, 505, 295, DIG. 2, 298; 606/42, 211

[56] References Cited

U.S. PATENT DOCUMENTS

| | | | |
|---|---|---|---|
| 3,700,836 | 10/1972 | Rackson | 200/505 X |
| 4,034,761 | 7/1977 | Prater et al. | 200/505 X |
| 4,343,973 | 8/1982 | Main | 200/516 |
| 4,552,143 | 11/1985 | Lottick | 200/293.1 X |
| 4,619,258 | 10/1986 | Pool | 200/505 X |

FOREIGN PATENT DOCUMENTS 260715 10/1989 Japan ............................ 200/293.1

*Primary Examiner*—Renee S. Luebke

[57] ABSTRACT

An electrosurgical handpiece for accommodating an assortment of different-sized electrodes having hollow shanks and provided with means for supplying suction adjacent the electrode tip for simultaneous removal of liquids or gasses. The handpiece can be fitted with a removable finger switch activator which can also be attached to other objects for the surgeon's convenience. Means for controlling the suction pressure at the electrode tip is also provided.

11 Claims, 7 Drawing Sheets

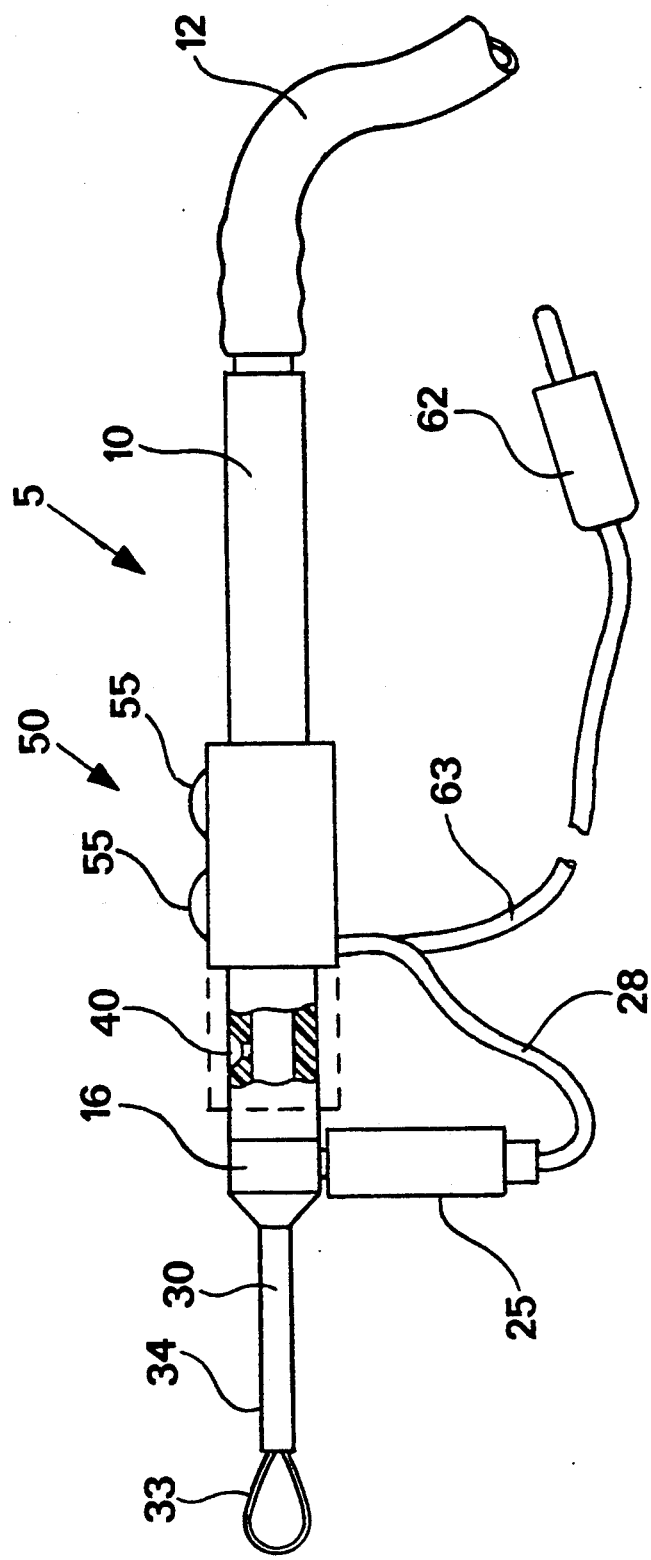
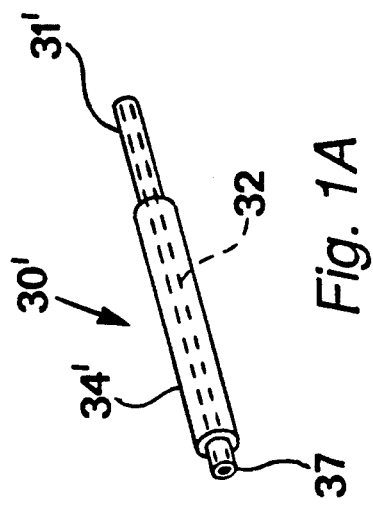
Fig. 1
Fig. 1A

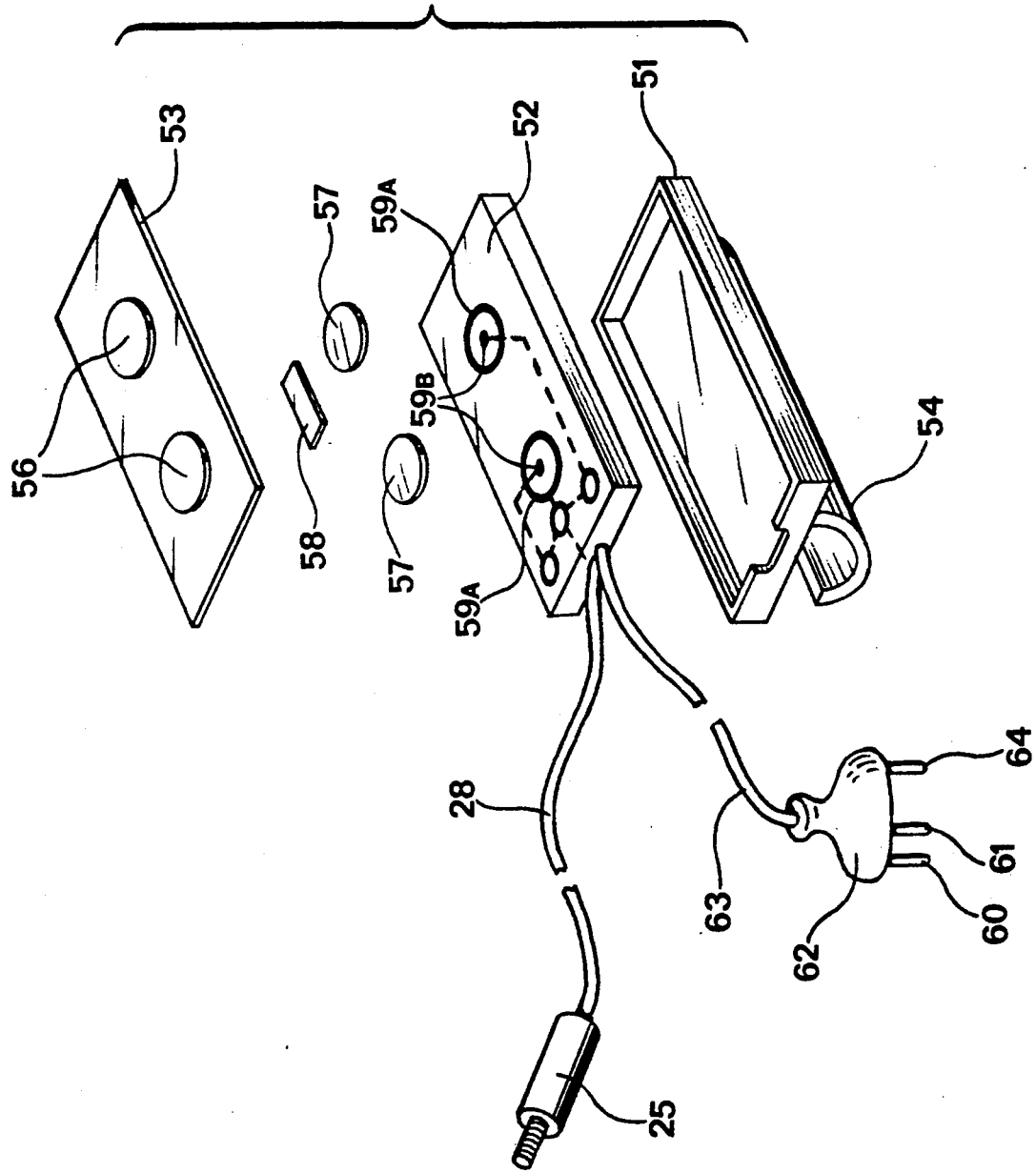

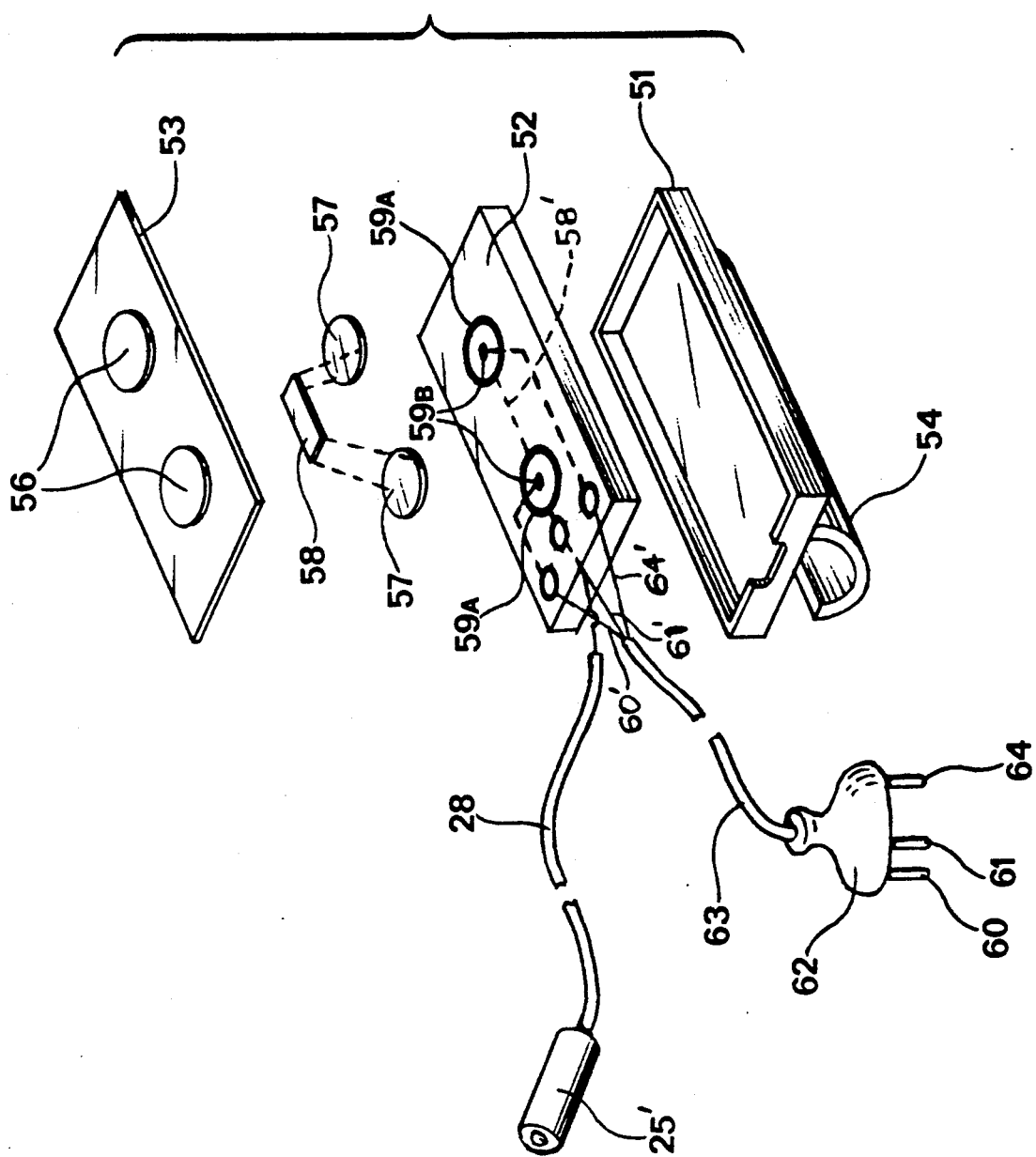

FINGER SWITCH FOR ELECTROSURGICAL HANDPIECE

This application is a division of application Ser. No. 07/711,860, filed Jun. 7, 1991, now U.S. Pat. No. 5,196,007.

This invention relates to an electrosurgical handpiece and an activator for an electrosurgical handpiece.

BACKGROUND OF THE INVENTION

Electrosurgery is a common procedure for dentists, doctors, and veterinarians. Electrosurgical handpieces are commercially available that will accommodate a wide variety of electrode shapes and sizes, such as needles, blades, scalpels, balls and wire loops. Also, multifunction electrodes are available. For example, the Ellman company makes available a suction coagulator. This is an instrument that can be connected to a source of electrosurgical energy and that provides the electrode in the form of a hollow tube with an exposed tip. By connecting a suction source to the hollow tube, blood and other liquids at the operative field can be drawn out while simultaneously bleeding capillaries can be coagulated electrosurgically. This instrument has limitations, since the electrode is permanently attached to its handle. Thus, if the dentist or doctor desires to change the size or length of the electrode, it is necessary to substitute a new instrument. Another drawback is that this instrument is designed for use with a standard foot activator. There are many practitioners who now prefer finger activators, as it gives them greater tactile feel of the instrument during the procedure. A further limitation is that the degree of suction cannot be controlled.

We are also joint inventors of an electrosurgical adaptor which can be connected to an electrosurgical mainframe and into which can be plugged a finger switch handpiece that can operate the equipment in place of the usual foot switch. See U.S. Pat. No. 4,463,759. This unit is also available from the Ellman Company. While the finger switch handpiece described in this patent and available commercially will receive electrodes of varying shapes and sizes, it does not allow suction to be made available at the electrode tip for combined suction-coagulation. Another drawback is that the finger activator is integral with the handpiece. There may be situations where it would be extremely useful to be able to separate the electrosurgical and the switch functions for the convenience of the surgeon.

SUMMARY OF THE INVENTION

An object of the invention is am electrosurgical handpiece that can accept multiple electrodes and that is capable of providing suction at the operative field for combined liquid or gas removal and electrocoagulation or electrocutting.

Another object of the invention is a finger switch activator for an electrosurgical handpiece that can be attached to any location or instrument near the surgical sight convenient to the surgeon.

A further object of the invention is an electrosurgical handpiece capable of providing combined liquid or gas removal and electrocoagulation and that is configured to cooperate with a removable finger switch activator.

According to one aspect of the invention, an electrosurgical handpiece is provided that is adapted to receive a suction hose and provide suction at a working end of the handpiece which can removably receive a hollow electrode capable of performing an electrosurgical function. In addition, means are provided for controlling the degree of suction available at the electrode tip. A preferred control means is simply a hole communicating with the suction passageway and terminating at the surface of the handpiece at a position convenient to the surgeon's finger. By covering and uncovering the hole, the surgeon can control the degree of suction available at the electrosurgical electrode.

In accordance with a preferred embodiment of this aspect of the invention, the handpiece is provided with a removable nose piece that will allow different sizes of electrodes to be accommodated with different sizes of nose pieces.

According to another aspect of the invention, a novel finger switch activator is provided that can be removably mounted on the electrosurgical handpiece of the invention, as well as on other surfaces or instruments. The activator can be plugged into the adaptor described in the referenced patent as well as to other standard electrosurgical mainframes, and can be connected to the electrosurgical handpiece of this invention as well as to other handpieces. The novel activator can be positioned at any location convenient to the surgeon to provide to the surgeon complete control of the power output from the electrosurgical instrument during surgery. This arrangement will prove of enormous benefit not only to the common electrosurgical procedures, but also to the newer fiber optic surgery such as laparoscopy where tactile feel is of the utmost importance.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

BRIEF DESCRIPTION OF THE DRAWINGS

In the drawings:

FIG. 1 is a plan view of an electrosurgical handpiece according to the invention fitted with a finger switch activator according to the invention;

FIG. 1A is a plan view of a modified electrode for use with the handpiece of FIG. 1;

FIG. 5 is an exploded view showing the interior construction of the finger switch activator of FIG. 4A;

FIG. 5A is a view similar to FIG. 5 showing the interior construction in more detail and with a different handpiece connector.

DETAILED DESCRIPTION OF THE PREFERRED EMBODIMENTS

Figure 2:
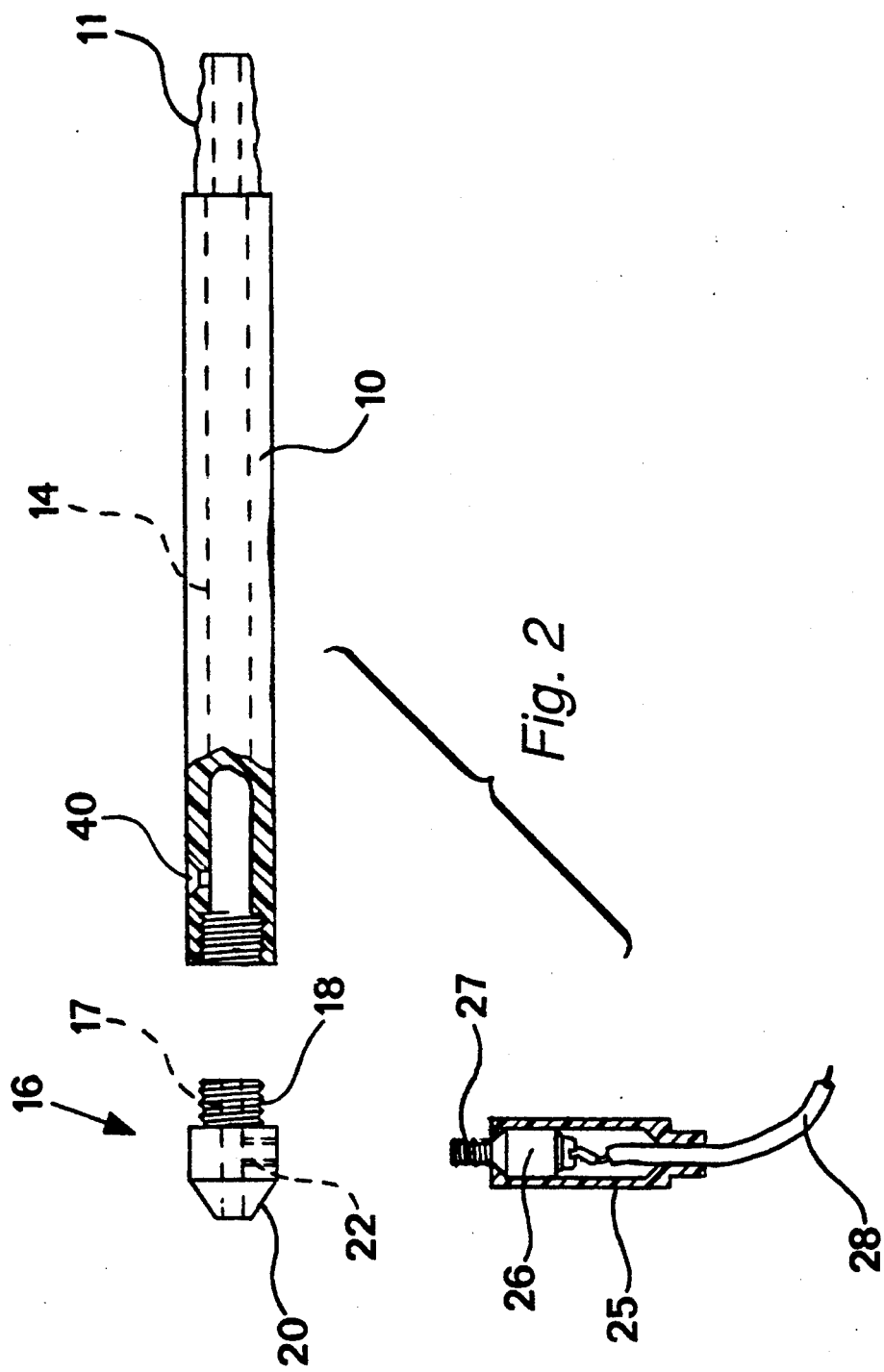
FIG. 2 is an exploded, cross-sectional view of the electrosurgical handpiece of FIG. 1.

FIG. 1 shows a preferred embodiment combining an electrosurgical handpiece 5 and finger switch activator 50 of the invention. The handpiece 5 comprises a straight, elongated, round handle 10 made, for example, of Delrin plastic. It comprises at its right end a tapered part with cylindrical ridges 11 which is dimensioned to receive and hold a standard suction hose 12 which can be removably attached to the end 11. The handpiece 5 has a bore 14 extending completely through it and at the opposite end of the handpiece terminates in an internal screw thread 15. Screwed into the latter is a removable nose or front piece 16, also, for example, of Delrin plastic, which also has a bore 17 extending completely through it. The nose piece 16 comprises a reduced diameter threaded portion 18 for engaging the threaded portion 15 of the handle 10, a knurled outer section 19, and a tapered snout 20. A threaded opening 22 extends through the side of the section 19 all the way to its bore 17.

The side opening 22 is configured to be engaged by a connector 25 having an internal metal insert part 26 with an external thread 27 for engaging the threaded side opening 22 in the nose piece 16. The rear of the metal insert 26 has an internal thread for receiving the threaded end of an internal conductor of an electrical cable 28.

The bore 17 of the nose piece 16 is sized to receive the metal shank 31 of an electrosurgical electrode 30. Conventional electrodes frequently come in different-sized shanks, for example, 1/16", 3/32", or 150". To accommodate the different sized electrodes, two or more nose pieces 16 can be provided, each with a different sized bore 17 to receive and hold the electrode shank 31 of different sized electrodes, and the appropriate nose piece 16 screwed into the handle 10 for the electrode 30 the surgeon intends to use. In this way, each bore 17 can be custom sized to provide a friction fit with the shank 31 of any sized electrode. Alternatively, the bore 17 can be sized to accommodate the largest shank size, and the connector 25 can be used to clamp the electrode in place in the bore by screwing it in the threaded hole 22 until the threaded front end 27 engages and pushes the shank 31 tight up against the bore wall to fix its position. In either case, an electrical connection is established between the electrode conductive portion 31 and the cable 28 when the connector is assembled.

The conductive portion or shank 31 of the electrode is hollow, having a bore 32 extending completely through it which communicates with the bore 17 of the nose piece 16 and the bore 14 of the handle 10. The particular electrode 30 shown in FIG. 1 has an active or working end in the form of a wire loop 33 whose ends are held in electrical engagement with the metal shank 31 by a protective insulating sleeve 34 shrunk around the latter. In operation, when electrosurgical energy is applied to the cable 28 and passed through to the electrode working end 33, soft tissue can be cut by the surgeon. This procedure tends to produce smoke, which may obscure the surgeon's vision. By applying suction via the tube 12, that suction will be passed through to the open end 36 of the hollow shank 31, and will draw in any smoke generated during tissue cutting with the adjacent wire end 33.

A modified form of electrode 30' is shown in FIG. 1A. In this case, the working end of the electrode is a short exposed end 37 of the hollow metal shank 31' which is elsewhere covered with the protective tube 34'. This electrode 30' would be useful as a combined liquid remover and capillary coagulator. When electrosurgical energy is applied to the electrode, by using the exposed tip 37 of the electrode, capillaries can be cauterized while simultaneously any blood or other liquids present at the site can be suctioned off and removed.

It is often desirable for the surgeon to be able to control the degree of suction applied in the operative field by the handpiece. This is accomplished according to the invention by providing in the handle 10 a side hole 40 which extends radially through the side wall into communication with the suction bore 14. This side opening 40 acts as a suction bypass. When left uncovered, most of the suction pressure is relieved at the side hole 40, and only a small fraction is available at the electrode end. The side hole 40 is positioned such that the surgeon can easily place a finger over the hole 40, blocking air flow through it. In this case, the full suction pressure will be available at the electrode end. As will be shown later, a slidable member can be provided on the handle 10, and slid by the user over the hole 40 when full suction pressure is desired at the operative site for an extended period of time.

The cable 28 can be terminated at its end remote from the connector 25 with a standard banana plug that can be plugged directly into the electrosurgical mainframe, and thus the electrosurgical energy furnished at the electrode working end will be determined by the mainframe controls and a conventional footswitch. However, most surgeons prefer hand control of the electrosurgical energy, as was explained in the earlier referenced patent. The present invention also contemplates a finger switch activator 50 adapted for an electrosurgical handpiece 5 of the type illustrated in FIG. 1 as well as other conventional handpieces.

Figure 4A:
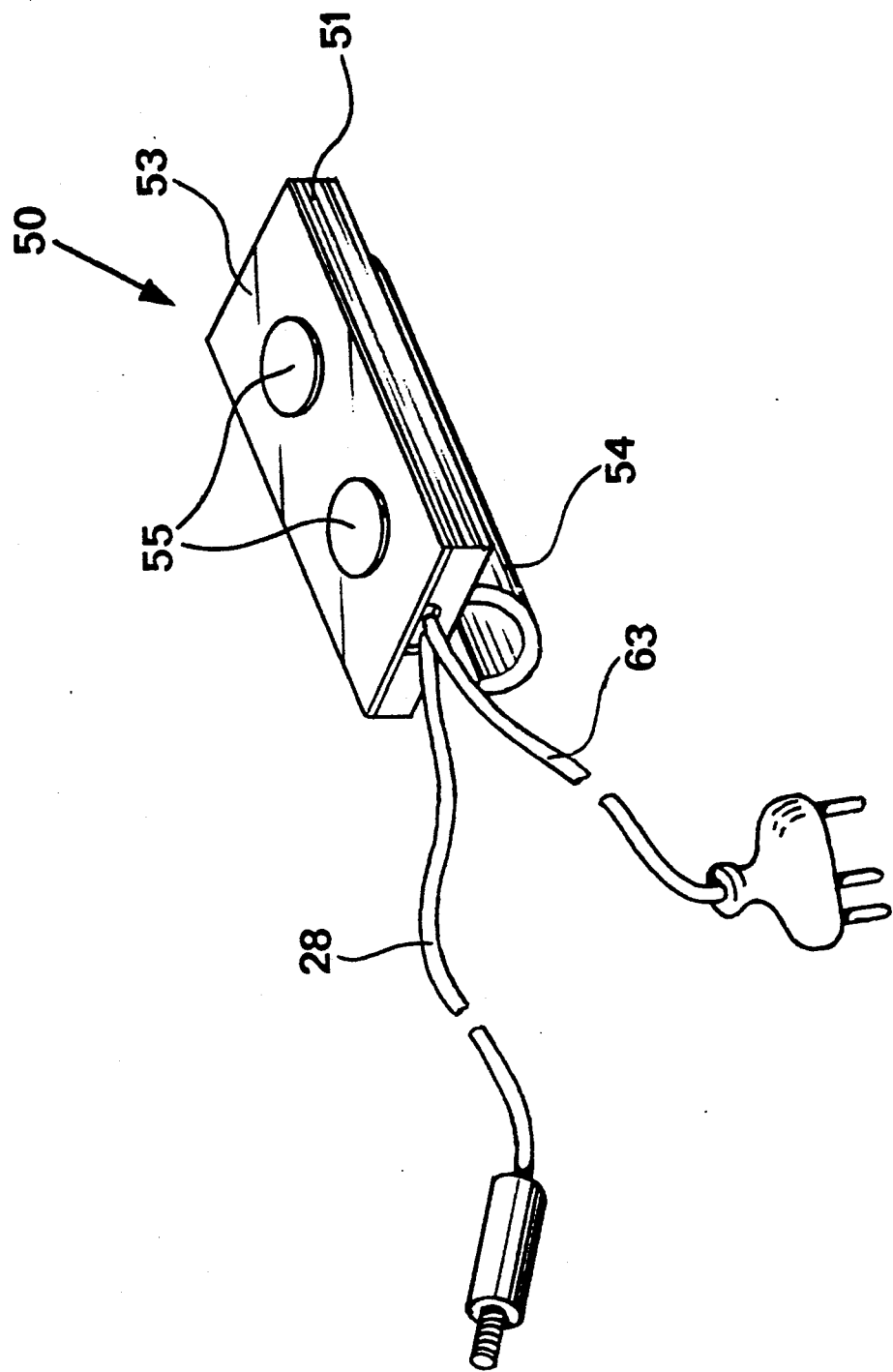
FIG. 4A is a perspective view of one form of the finger switch activator according to the invention.

One form of finger switch activator 50 according to the invention is shown in working position in FIG. 1, separately in FIG. 4A, and in an exploded view in FIG. 5. It comprises a generally thin, rectangular housing 51 supporting a printed circuit board 52 and a cover plate 53. The housing 51 is provided with means for attaching or holding the activator 50 onto the handpiece 5. In this embodiment, such means comprises an arc-shaped member 54 sized to slide around the barrel-shaped handle 10 and thus clamp the activator 50 to the handle 10. The cover plate 53 contains two insulating, flexible protrusions 56 which house electrical dome contacts 57 interconnected by an electrically-conductive strip 58 to form two button switches 55. In the more detailed view in FIG. 5A, the printed circuit board 52 has a pattern of electrical lines such that depressing a protrusion 56 and thus the underlying dome contact 57 will cause an electrical connection to be established between one of two pairs of elements 59A, 59B of the printed circuit. In the assembled condition, the dome contacts 57, interconnected by the conductive strip 58, contact the conductive rings 59A which thus become interconnected, indicated by dashed line 58' in FIG. 5A. The circuit is such that the conductive rings 59A connect to the cable 28 which feeds power to the handpiece electrode, whereas the dot conductors, 59B connect in turn to one terminal 60, 64 of a connector 62 via a multi-conductor electrical cable 63. The remaining terminal is also connected to the conductor rings 59A. The cable conductors 60', 61', 64' are connected, respectively, to the terminals 60, 61, 64. The connector 62, as will be evident, corresponds to the connector of the cable 41 of the handpiece disclosed in the referenced U.S. Pat. No. 4,463,759, and thus can be plugged into the adaptor described in that patent to make available, by actuation of one or the other of the button switches 55, electrosurgical energy for cutting or for coagulation. It will also be appreciated that a third or more buttons can be readily added to the activator 50 to provide in addition mixed or fulguration currents if desired. FIG. 5A also shows that the connector 25 of FIG. 5 has been replaced by a conventional female banana connector 25' for receiving a standard banana plug of a conventional handpiece.

In operation, as shown in FIG. 1, the finger switch activator 50 mounts on the electrosurgical handpiece handle 10, by simply sliding it on to the latter. It can be easily positioned to any location convenient to the surgeon where he or she can easily manipulate the button switches 55 with one or two fingers to control the application of electrosurgical energy to the electrode. As previously indicated, the finger switch activator can be slid over the suction bypass opening 40, shown in dashed lines, for continuous full suction pressure at the electrode end. In the form shown in FIG. 1, the cable 28 connects to the handpiece connector 25, and the cable 63 connects to the patented adaptor or other source of electrosurgical energy.

Figure 4B:
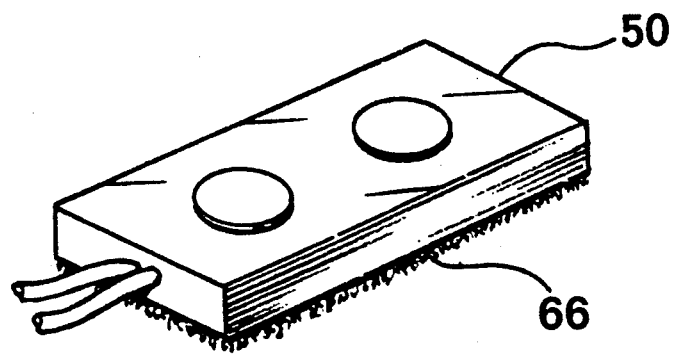
FIGS. 4B–4D are perspective views of modifications of the finger switch activator according to the invention.
Figure 4C:
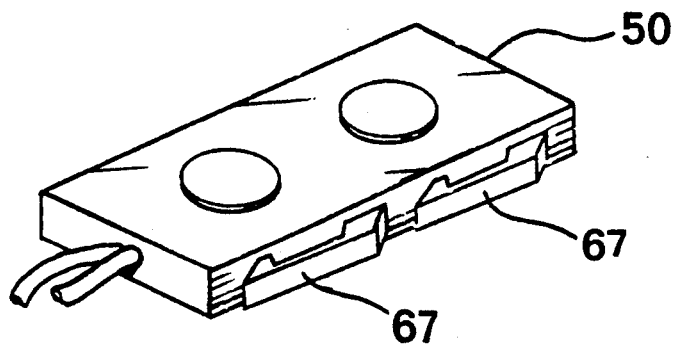
Figure 4D:
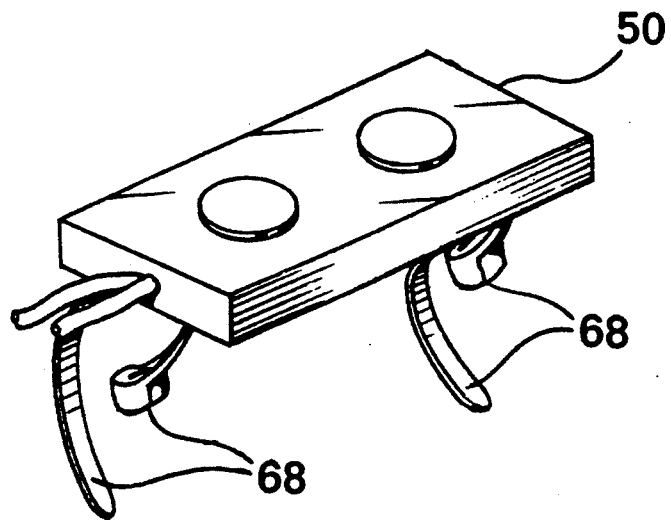

Among the advantages of the finger switch activator according to the invention is that it can be attached to all standard foot activated accessories transforming them into finger-activated devices. Moreover, it can be attached to any electrosurgical instrument which offers a finger switch modality. Moreover, since it is removable, it can be applied or attached to any location or instrument near the surgical sight convenient for the surgeon. The use of the arc-shaped clamping member 54, while preferred for barrel-shaped handpieces, is not necessary. Any convenient way of attaching the finger switch activator, which is small, lightweight, and slim, can be used. FIGS. 4B, 4C, and 4D show examples of modified attachment means. In FIG. 4B, VELCRO 66 can be provided along its bottom surface to cooperate with matching VELCRO on the attachment surface. FIG. 4C shows dual clips 67 which can cooperate with slotted recesses or pockets. FIG. 4D shows the use of tie straps 68 for tying the device 50 around an object. Other attachment means will be obvious to those skilled in this art.

Figure 3:
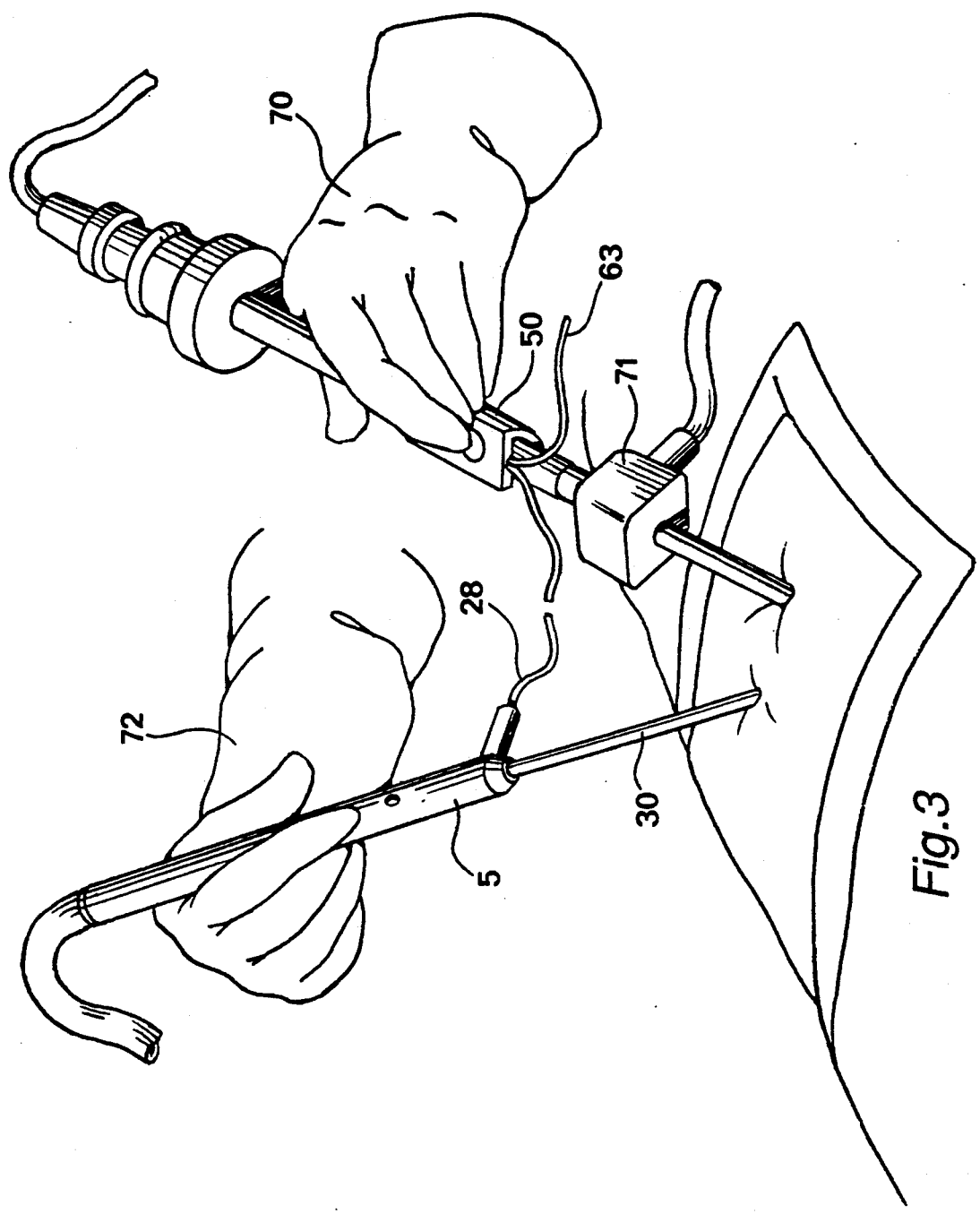
FIG. 3 illustrates use of the devices of FIG. 1 in a laparoscopy procedure.

An important application of this capability is in fiber optic surgery (surgery performed through a small incision with all of the procedures accomplished through small diameter tubes with long accessories). In this environment, it may become impractical to utilize the standard fingerswitch or foot control due to loss of dexterity, additional wires, and reduced control. The activator according to the invention can be placed on any of the instruments used by the surgeon for increased versatility. FIG. 3 illustrates a typical fiber optics procedure, for example, laparoscopy, in which one hand 70 of the surgeon manipulates the fiber optics viewer 71 while the other hand 72 holds an electrosurgical handpiece 5 like the one illustrated in FIG. 1. In this case, the electrode 74 used would be approximately 16" long. The finger switch activator 50 for the electrosurgical handpiece is shown in this instance mounted on the fiber optics instrument 71, as the surgeon finds it more convenient to use a finger on his right hand 70 to activate the electrosurgical handpiece. Similarly, if desired, the finger switch activator is small enough so that it can be mounted instead on one finger and activated by another finger, or by pressing the button switches 55 against a hard surface.

While the parts of the electrosurgical handpiece, made up of metal and Delrin, are autoclavable, the device is sufficiently simple that it can be manufactured at very low cost with a less expensive plastic and thus can be made disposable. The finger switch activator cannot be autoclaved, which might damage the electrical contact surfaces, but again is relatively simple in construction and can also be made inexpensively and thus disposable.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrical device for energizing an electrosurgical handpiece, comprising:
   a finger switch having a housing containing a printed circuit board,
   at least one finger actuator means accessible on the outside of the housing and when depressed establishing via the printed circuit board an electrical connection between first and second conductors on the printed circuit board,
   a first electrical cable connected to the finger switch and its first conductor for supplying electrosurgical energy,
   a second electrical cable connected to the second conductor and having means for electrical connection to the electrosurgical handpiece, whereby electrosurgical energy will be made available at an electrode mounted in the handpiece in response to actuation of the finger actuator means on the finger switch,
   means for removably mounting the finger switch on an object.

2. An electrical device as claimed in claim 1, wherein the first electrical cable contains plural conductors for supplying different kinds of electrosurgical energy, and further comprising at least a second finger actuator means which when depressed establishes an electrical connection between a third conductor and the second conductor, said first and third conductors being connected to different conductors in the first cable.

3. An electrical device as claimed in claim 1, wherein the removable mounting means comprises an arcuate extension of the housing configured to clamp on and over the object, said mounting means being slidable over the surface of the object when clamped thereon.

4. An electrical device as claimed in claim 1, wherein the removable mounting means comprises clips on the housing.

5. An electrical device as claimed in claim 1, wherein the removable mounting means comprises means for tying the housing to the object.

6. An electrical device as claimed in claim 1, wherein the removable mounting means comprises VELCRO means for attaching same to the object.

7. An electrical device as claimed in claim 1, wherein the finger actuator means comprises an electrical dome contact.

8. An electrical device as claimed in claim 1, wherein the housing comprises a generally thin, generally rectangular member.

9. An electrical device as claimed in claim 1, wherein the means for electrical connection on the second electrical cable comprises a connector for connecting to a mating connector on the handpiece.

10. An electrical device for energizing an electrosurgical handpiece, comprising:

a finger switch having a housing containing a printed circuit board, at least one finger actuator means accessible on the outside of the housing and when depressed establishing via the printed circuit board an electrical connection between first and second conductors on the printed circuit board, a first electrical cable connected to the finger switch and its first conductor and having a first connector for connecting to an electrosurgical machine for supplying electrosurgical energy to the first terminal, a second electrical cable connected to the second conductor and having a second connector for electrical connection to a connection on the electrosurgical handpiece, whereby electrosurgical energy will be made available at an electrode mounted in the handpiece in response to actuation of the finger actuator means on the finger switch, means for removably mounting the finger switch on an object, said removable mounting means being free of electrosurgical energy whether or not the finger actuator means is depressed.

11. An electrical device as claimed in claim 10, wherein the removable mounting means consists only of non-conductive means for tying the housing to the object.

* * * * *